United States Patent [19]
Johnson et al.

[11] Patent Number: 5,304,146
[45] Date of Patent: Apr. 19, 1994

[54] MEDICAL APPLIANCE SECURING DEVICE

[76] Inventors: Melissa C. Johnson, 758 Main St., Leominster, Mass. 01453; Philip E. Baker, 5 Fox Hill La., Norfolk, Mass. 02056; Joseph Giovino, 545 Goodrich St., Lunenburg, Mass. 01462

[21] Appl. No.: 965,748

[22] Filed: Oct. 23, 1992

[51] Int. Cl.$^5$ .................................. A61M 25/02
[52] U.S. Cl. ............................ 604/180; 128/DIG. 26
[58] Field of Search .................. 604/174, 179, 180; 128/DIG. 26, DIG. 15; 24/302

[56] References Cited

U.S. PATENT DOCUMENTS

| | | |
|---|---|---|
| D. 243,477 | 2/1977 | Lutruzzula et al. ........ 128/DIG. 26 |
| 2,669,231 | 2/1954 | Fisher . |
| 3,160,158 | 12/1964 | Rayhart . |
| 3,288,136 | 11/1966 | Lund . |
| 3,430,300 | 3/1969 | Doan . |
| 3,677,250 | 7/1972 | Thomas . |
| 3,726,280 | 4/1973 | Lacount . |
| 3,765,421 | 10/1973 | Poprik . |
| 3,782,383 | 1/1974 | Thompson et al. . |
| 3,826,254 | 7/1974 | Mellor . |
| 3,834,380 | 9/1974 | Boyd . |
| 3,878,849 | 4/1975 | Muller et al. . |
| 3,990,454 | 11/1976 | Schlesinger . |
| 4,074,397 | 2/1978 | Rosin ................. 128/DIG. 26 |
| 4,088,136 | 5/1978 | Hasslinger et al. ........ 128/DIG. 26 |
| 4,096,863 | 6/1978 | Kaplan et al. ............ 128/DIG. 26 |
| 4,122,857 | 10/1978 | Haerr ................. 128/DIG. 26 |
| 4,129,128 | 12/1978 | McFarlane ............. 128/DIG. 26 |
| 4,165,748 | 8/1979 | Johnson . |
| 4,336,806 | 6/1982 | Eldridge, Jr. . |
| 4,416,664 | 11/1983 | Womack ............... 604/174 |
| 4,445,894 | 5/1984 | Kovacs . |
| 4,484,914 | 11/1984 | Brown ................. 604/180 |
| 4,569,348 | 2/1986 | Hasslinger . |
| 4,571,245 | 2/1986 | Hubbard et al. ......... 604/179 |
| 4,591,356 | 5/1986 | Christie ............... 604/179 |
| 4,617,017 | 10/1986 | Hubbard et al. ......... 604/179 |
| 4,639,980 | 2/1987 | Peterson ............. 128/DIG. 26 |
| 4,700,432 | 10/1987 | Fennell ................ 24/16 R |
| 4,702,736 | 10/1987 | Kalt et al. ............ 604/180 |
| 4,726,716 | 2/1988 | McGuire .............. 604/180 |
| 4,898,587 | 2/1990 | Mera .................. 604/174 |
| 4,962,757 | 10/1990 | Stefan ............... 128/DIG. 26 |
| 4,976,700 | 12/1990 | Tollini et al. ........ 604/180 |
| 5,000,741 | 3/1991 | Kalt .................. 604/180 |
| 5,019,050 | 5/1991 | Lynn et al. ........... 604/179 |
| 5,100,393 | 3/1992 | Johnson .............. 604/180 |
| 5,147,322 | 9/1992 | Bowen et al. .......... 604/180 |

FOREIGN PATENT DOCUMENTS

2233902 1/1991 United Kingdom ............. 604/180

Primary Examiner—John G. Weiss
Attorney, Agent, or Firm—Kriegsman & Kriegsman

[57] ABSTRACT

A device for securing a generally tubular member of a medical appliance to a support surface. In one embodiment, the device comprises an anchoring patch, the anchoring patch including a first segment and a second segment and having a top surface and a bottom surface. The bottom surface is coated with an adhesive for attaching the anchoring patch to the support surface. A pair of flexible retaining tabs extend from and interconnect the inner edges of the first and second segment, the flexible retaining tabs being of sufficient length to helically wrap around the circumference of the generally tubular member and contact the top surface of the anchoring patch. First fasteners are secured to the free ends of the flexible retaining tabs and a pair of complementary fasteners are spaced outwardly relative to the tabs and are secured to the top surface of said anchoring patch. A generally tubular member may be retained in the device either by helically wrapping the flexible retaining tabs around the circumference of the generally tubular member and then coupling together the fasteners or by positioning the generally tubular member between the flexible tabs and the complementary fasteners and looping the retaining tabs over the generally tubular member and then coupling together the fasteners.

17 Claims, 11 Drawing Sheets

MEDICAL APPLIANCE SECURING DEVICE

BACKGROUND OF THE INVENTION

The present invention relates generally to medical appliance securing devices and more particularly to a new and novel medical appliance securing device.

Various medical devices, or portions thereof, are shaped as generally tubular members, such as, for example, catheters, thermometers, i.v. tubing and various types of electrical wires. There is often a need to secure such devices to or near a patient's body so that they can appropriately function. In particular, catheters are medical appliances often used in surgical procedures for transporting various types of fluids to and from the body of a patient. Catheters are generally long, tubular conduits made from flexible materials and, in use, typically extend from the patient to a nearby stationary receptacle or to a source of fluid. As can readily be appreciated, it is often necessary to limit lateral and/or longitudinal movement of the medical appliance tube relative to the patient's body to insure proper placement and functioning of the catheter, as well as to offer some degree of comfort and mobility for the patient. In particular, some medical procedures require the application of a tensile force, known as traction, to the catheter, thus making it particularly necessary to firmly secure the catheter tube in its longitudinal direction.

To provide the necessary restraint, practitioners initially used strips of conventional, medical-grade adhesive tape to secure the catheter tube directly to the patient's skin. This method proved unsuccessful, however, because the tape would tend to become loose, and because each time the catheter was adjusted or temporarily removed, it was necessary to also remove the adhesive tape from the patient's skin, thus causing significant irritation and discomfort.

Various types of catheter securing devices were subsequently developed to provide the desired restraint and to overcome the disadvantages associated with the use of strips of adhesive tape. In U.S. Pat. No. 3,677,250 to Thomas, issued Jul. 18, 1972, there is disclosed adhesive tape for anchoring to a given substrate, elongated members such as surgical tubing or the like, consisting of at least one anchoring tab portion with strap means extending from the tab portion for wrapped engagement with the tubing, the strap means being connected to the tab portion in a manner to prevent peeling and separation of the tab portion from the substrate upon tensioning of the strap means, the tape being selectively used in a manner to (1) restrain the tubing against both lateral and longitudinal movement relative to the substrate; or (2) restrain the tubing only against lateral movement while permitting longitudinal movement relative to the substrate.

In U.S. Pat. No. 3,834,380 to Boyd, issued Sep. 10, 1974, there is disclosed a holder for tubular items, particularly equipment used during intravenous injections, such as infusion tubing or the hub of an injection cannula. The holder comprises a strip of adhesively-backed tape and a longitudinally split, elongate, cylindrical, clamping tube of flexible and preferably resilient plastic material securely attached to the top of the tape. A latch for positively keeping the clamping tube closed about a received item may be provided, preferably in the form of a securement flap attached to the clamping tube at one side thereof and interlocking means having component parts attached, respectively, to the securement flap and at the opposite side of the clamping tube. For holding both an injection cannula and infusion tubing during the administering of an intravenous liquid, two or more clamping tubes may be provided in juxtaposed position on a single piece of tape.

In U.S. Pat. No. 4,165,748 to Johnson, issued Aug. 28, 1979, there is disclosed a simple easily applied one-piece catheter tube holder originally made flat and comprising two main parts having adhesive thereon for temporary attachment to the limb of a patient, there being a narrow bridge also provided with adhesive and connecting the two main parts, said narrow bridge being foldable in the center thereof to form a double member, and having fasteners such as snap fasteners or Velcro for holding the same in position to releasably hold the catheter tube in the desired orientation to the patient.

In U.S. Pat. No. 4,445,894 to Kovacs, issued May 1, 1984, there is disclosed a band for securing a catheter or similar device to a limb of a human comprising a stretchable primary strap adapted to encircle a limb. A part of the strap is made of a soft looped fabric and the strap also carries a male Velcro-type fastening material which cooperates with the looped fabric to enable the strap to be secured in place about the limb. A second strap made of a flexible material is secured, hooks up, intermediate its ends to the central portion of the primary strap on the looped fabric. The secondary strap is made of a male Velcro-type fastening material, and each end of the secondary strap is designed to be looped over and encircle the catheter or similar device and attach to the looped fabric to hold the catheter or similar device securely in place on the limb.

In U.S. Pat. No. 4,569,348 to Hasslinger, issued Feb. 11, 1986, there is disclosed a separable fastening device for supporting a medical device such as a catheter tube or the like to a limb of a patient. The device includes a first and a second strap member. The first strap member includes a flexible first strap section formed of a knitted textile material having upstanding from one surface a plurality of multifilamentary loop-like elements and a polyurethane foam substrate secured to the opposite surface. The first strap member also includes a second strap section which is formed of a flexible tape member having upstanding from one surface a plurality of hook-like elements which matingly engage with the upstanding filamentary loop-like elements of the first section so as to be attachable thereto at the respective end portions to form a complete flexible first strap member. The second strap member includes a third strap section formed of a flexible tape member having an adhesive coating on one surface and a plurality of hook-like engaging elements on the opposite surface. The adhesive surface can be wrapped about the catheter tube and thereafter the hook-like elements can be matingly engaged with the loop-like elements of a portion of the first strap section. Upon encircling the first strap section about a limb and enfolding it over the the third strap section, the hook-like elements of the second strap section can matingly engage the loop-like elements of the first strap section to secure the catheter tube in relation to the limb.

In U.S. Pat. No. 4,617,017 to Hubbard et al., issued Oct. 14, 1986, there is disclosed a personal catheter leg strap for the securement of any one of a plurality of differently sized catheter tubes, the strap including a first section of gauze type material and a second section of elastic type material joined together at a junction for wrapping about a limb. A Velcro-type strip attaches the two free ends of the first and second portions together. A catheter tube securing strap is attached at one end thereof to the junction and has two portions, of which one portion is narrower throughout its length. An orifice is disposed in the broad portion and is dimensioned such that the entire length of the narrow portion is insertable therein. The securing strap has a free end thereof wrapped around a catheter tube one revolution and inserted through the orifice. Within the one revolution, protruding members protrude inwardly into the exterior surface of the tube, firmly securing it to the strap. The strap is wrapped an additional approximately one-half revolution about the catheter tube and is attached at any of an infinite number of locations on the surface with the Velcro-type surface of the securing strap.

In U.S. Pat. No. 4,702,736 to Kalt et al., there is disclosed a clamp for holding an article to an object, the clamp including a base means for adhering the clamp to the object, a flap, securing means for securing the flap to the base means with the article positioned therebetween and resilient pad means having an adhesive surface for contacting the article. The securing means includes a first holding means for holding a first portion of the flap and a second holding means for holding a second portion of the flap. Both holding means may be releasable. The second holding means is spaced from the first holding means a sufficient distance along the flap for the article to lie between them. Resilient adhesive surfaces are provided on the flap and base means for contacting and adhering the article.

In U.S. Pat. No. 4,976,700 to Tollini, issued Dec. 11, 1990, there is disclosed a securing tape for securing to a patient's skin or to a support, a medical device such as tubing, a catheter, an intravenous needle or the like. The securing tape includes an elongated tape having base portions and a central tab formed integrally therewith, pressure-sensitive tape on the base portions and on an exposed window of the tab, and hook and pile fastener portions on opposite sides of the exposed adhesive on the tab and on the base portion facing the exposed adhesive.

In U.S. Pat. No. 5,147,322 to Bowen et al., issued Sep. 15, 1992, there is disclosed a medical appliance securing device for laterally and longitudinally securing generally tubular members having various diameters to any desired location on the surface of a patient's skin or other support. The invention comprises an anchoring patch having one surface coated with adhesive for bonding the device to a patient's skin or some other support. A retaining tab is connected to the anchoring patch and contains an aperture such that the retaining tab may be wrapped around the circumference of the tubular member, inserted through the aperture, and firmly secured to the anchoring patch through the use of fastening means.

SUMMARY OF THE INVENTION

It is an object of the present invention to provide a new and novel device for securing a generally tubular member of a medical appliance to a support surface.

It is another object of the present invention to provide a device as described above which permits the generally tubular member of a medical appliance secured thereby to be removed and reapplied without requiring removal of the device from the support surface.

It is yet another object of the present invention to provide a device as described above that is simply and economically constructed.

It is still another object of the present invention to provide a device as described above that may be used to limit either the lateral movement or the lateral and longitudinal movement of the generally tubular member of a medical appliance secured thereby.

It is still yet another object of the present invention to provide a device as described above that may be used to secure generally tubular members of various diameters.

Additional objects, as well as features and advantages, of the present invention will be set forth in part in the description which follows, and in part will be obvious from the description or may be learned by practice of the invention. The objects, features, and advantages of the invention may be realized and attained by means of the instrumentalities and combinations particularly pointed out in the appended claims.

In one embodiment of the invention, the device comprises an anchoring patch. The anchoring patch includes a first segment and a second segment and has a top surface and a bottom surface, the bottom surface being coated with an adhesive for attaching the anchoring patch to the support surface. A pair of elongated, flexible, retaining tabs extend from and interconnect the central portions of the inner edges of the first segment and the second segment of the anchoring patch, the retaining tabs each having a first end connected to the anchoring patch and a free end for contacting the anchoring patch. First fastening means are secured to the free ends of the retaining tabs and complementary fastening means are secured to the top surface of the first segment of the anchoring patch, the complementary fastening means being spaced outwardly relative to the retaining tabs.

The foregoing device may be used to secure a generally tubular member of a medical appliance to a support surface in at least any of the following three ways: (1) With the generally tubular member of the medical appliance positioned across the length of the first segment of the anchoring patch, the retaining tabs are wrapped around the circumference of the generally tubular member, and the first fastening means are brought into secure engagement with the complementary fastening means; (2) With the generally tubular member of the medical appliance positioned across the length of the second segment of the anchoring patch, the flexible retaining tabs are wrapped around the circumference of the generally tubular member, and the first fastening means are brought into secure engagement with the complementary fastening means; or (3) With the generally tubular member of the medical appliance positioned across the length of the first segment of the anchoring patch, the retaining tabs are looped over the generally tubular member, and the first fastening means are brought into secure engagement with the complementary fastening means.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings, wherein like reference numerals represent like parts.

DETAILED DESCRIPTION OF PREFERRED EMBODIMENTS

Figure 1:
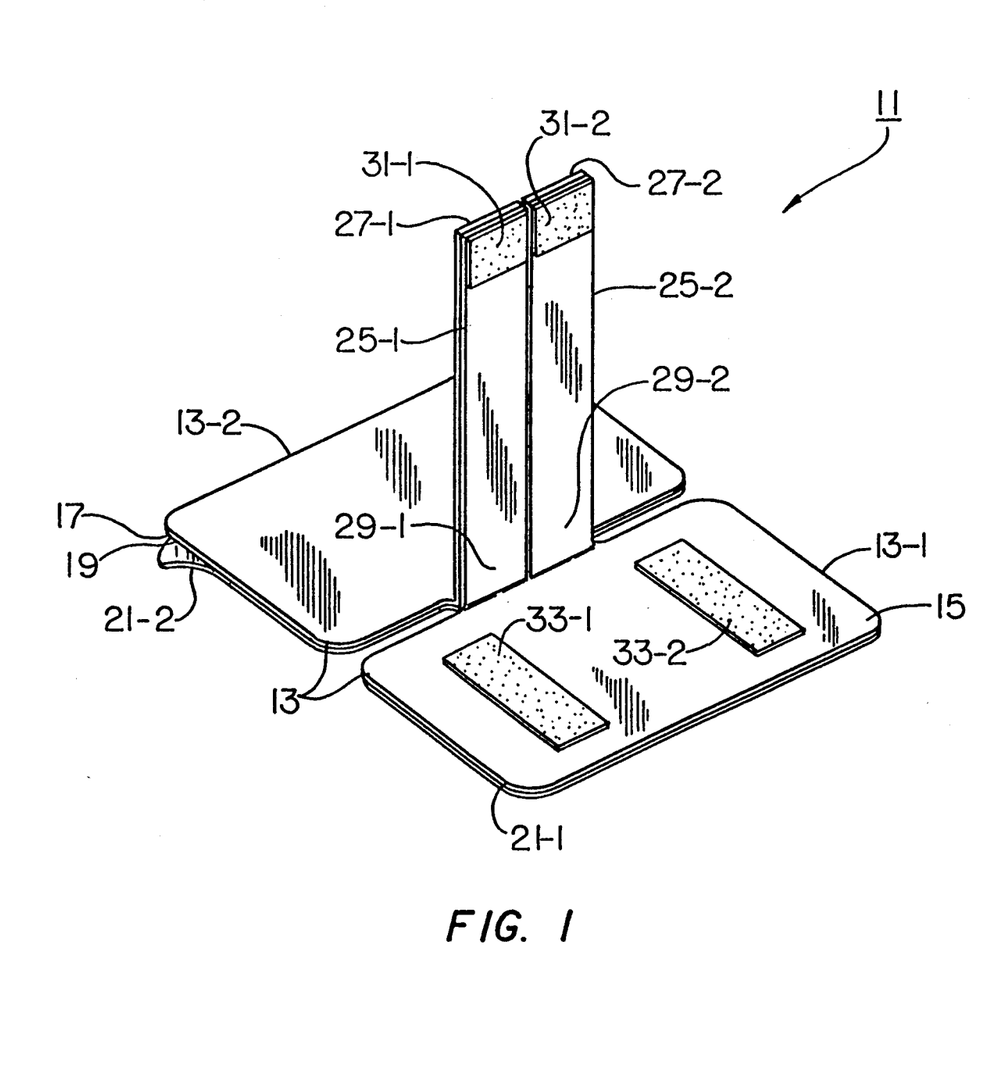
FIG. 1 is a perspective view of a first embodiment of a device constructed according to the teachings of the present invention for securing a generally tubular member of a medical appliance to a support surface.
Figure 2:
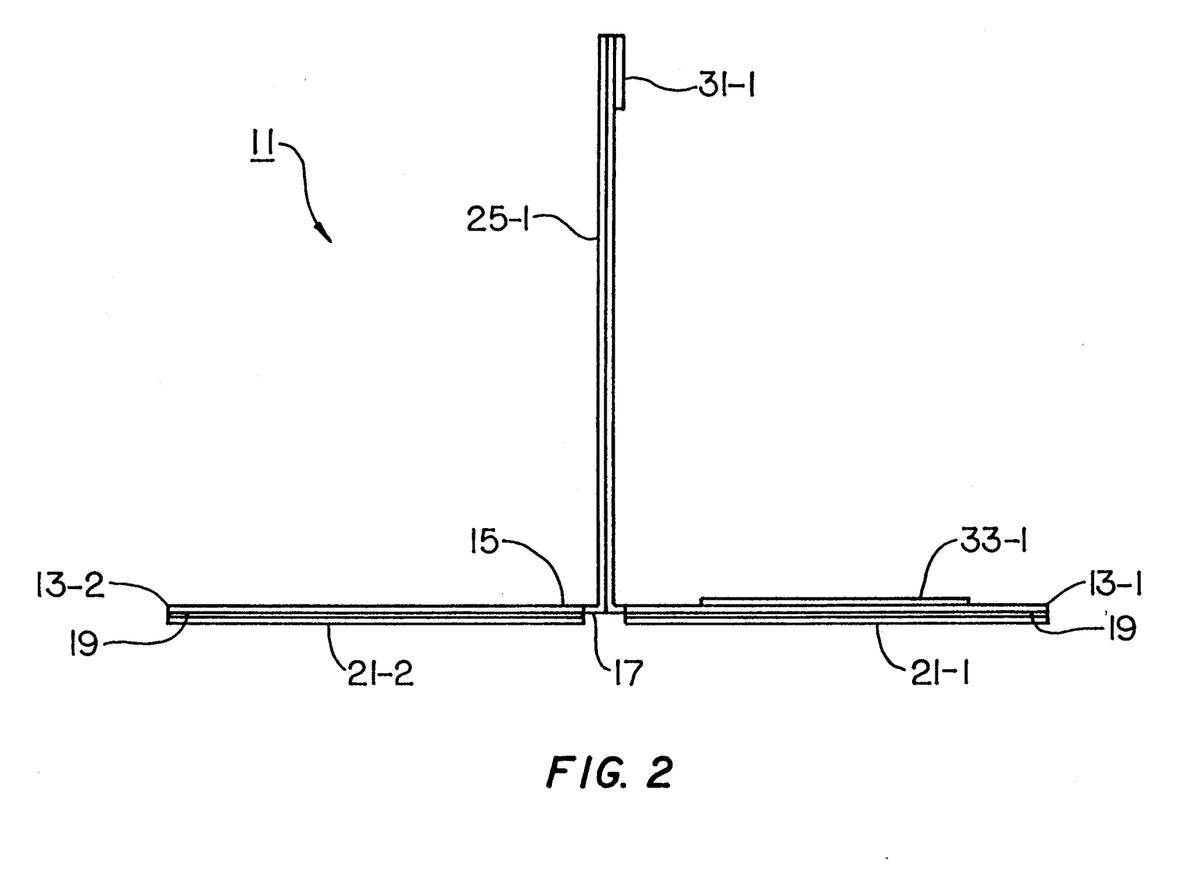
FIG. 2 is a side view of the device shown in FIG. 1.

Referring now to FIGS. 1 and 2, there is shown a first embodiment of a device constructed according to the teachings of the present invention for securing a generally tubular member of a medical appliance to a support surface, the device being represented generally by reference numeral 11.

Device 11 includes an anchoring patch 13. Anchoring patch 13 comprises a first segment 13-1 and a second segment 13-2 and has a top surface 15 and a bottom surface 17. Bottom surface 17 of anchoring patch 13 is coated with a pressure-sensitive adhesive 19, which in turn is covered by a pair of release liners 21-1 and 21-2. Release liners 21-1 and 21-2 may be peeled off to expose adhesive 19 on bottom surface 17 for bonding device 11 to a support surface, such as a patient's skin.

Device 11 also includes a pair of flexible retaining tabs 25-1 and 25-2 which extend from and which interconnect the inner edges of segments 13-1 and 13-2. Each tab 25 has a free end 27 and a connected end 29, connected end 29 being connected to the inner edges of segments 13-1 and 13-2. Tabs 25-1 and 25-2 are preferably integrally formed with anchoring patch 13, each tab 25 comprising a piece of material secured together in a superposed relation to form a double bridge member. Tabs 25-1 and 25-2 are of sufficient length so that they may be independently wrapped around the circumference of a tubular member and extended far enough to contact top surface 15 of anchoring patch 13.

First fastening means 31-1 and 31-2 are mounted on free ends 27-1 and 27-2, respectively, and face in the direction of first segment 13-1. Complementary fastening means 33-1 and 33-2 are spaced outwardly relative to first fastening means 31-1 and 31-2, respectively, and are mounted on top surface 15 of first segment 13-1. As can be seen, complementary fastening means 33-1 and 33-2 are elongated in shape and extend a substantial portion of the way across the width of first segment 13-1. In this manner, first fastening means 31-1 and 31-2 may be secured to complementary fastening means 33-1 and 33-2 at different points along their respective lengths to accommodate tubular members of various diameters.

Preferably, first fastening means 31 and complementary fastening means 33 are hook and loop fastening material, such as the material sold under the VELCRO trademark. Another type of fastening material may be resealable pressure-sensitive adhesive tape. Other fastening materials which permit repeated fastening and unfastening and which pemrit connection to be made at various positions will also be suitable.

To attach device 11 to a support surface S, such as a patient's skin, release liners 21-1 and 21-2 are peeled away from bottom surface 17 of anchoring patch 13, thereby exposing adhesive 19. Anchoring patch 13 is then pressed against the desired location on the patient's skin or other support until adhesive 19 securely bonds anchoring patch 13 to surface S. With device 11 thus secured to surface S, device 11 may be used in at least the three ways shown in FIGS. 3 through 5 to secure a generally tubular member T of a medical appliance to a support surface S.

Figure 3:
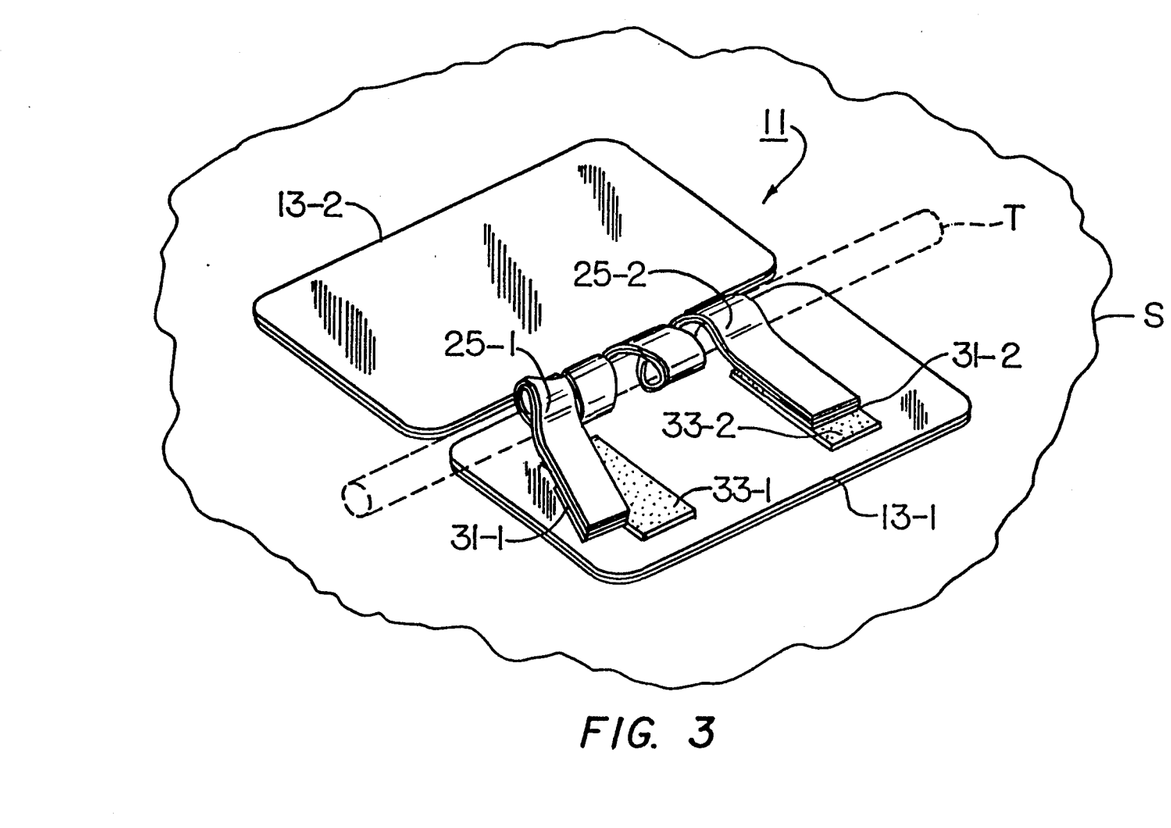
FIG. 3 is a perspective view showing a first way in which the device of FIG. 1 may be used to secure a catheter tube (shown in phantom) to a surface.

To use device 11 to secure generally tubular member T to a support surface S in the manner shown in FIG. 3, tubular member T is first positioned so that it extends across first segment 13-1. Tabs 25-1 and 25-2 are then independently wrapped in a generally helical or spiralling manner tightly around the circumference of tubular member T, and first fastening means 31-1 and 31-2 are brought into secure engagement with complementary fastening means 33-1 and 33-2, respectively.

Figure 4:
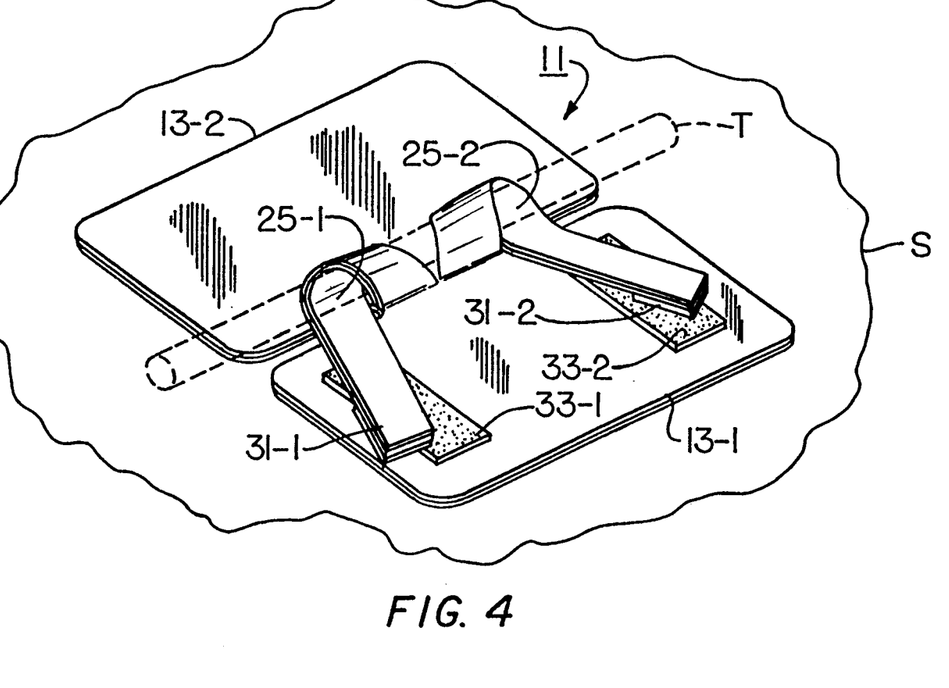
FIG. 4 is a perspective view showing a second way in which the device of FIG. 1 may be used to secure a catheter tube (shown in phantom) to a surface.

Alternatively, to use device 11 to secure generally tubular member T to a support surface S in the manner shown in FIG. 4, tubular member T is first positioned so that it extends across second segment 13-2. Tabs 25-1 and 25-2 are then independently wrapped in a generally helical or spiralling manner tightly around the circumference of tubular member T, and first fastening means 31-1 and 31-2 are brought into secure engagement with complementary fastening means 33-1 and 33-2, respectively.

When used as shown in FIGS. 3 and 4, device 11 tends to restrain movement of the generally tubular member T in both the lateral and longitudinal directions. This is because retaining tabs 25-1 and 25-2 are typically wrapped tightly around the circumference of the tubular member, thereby exerting a firm grip on the tubular member.

Figure 5:
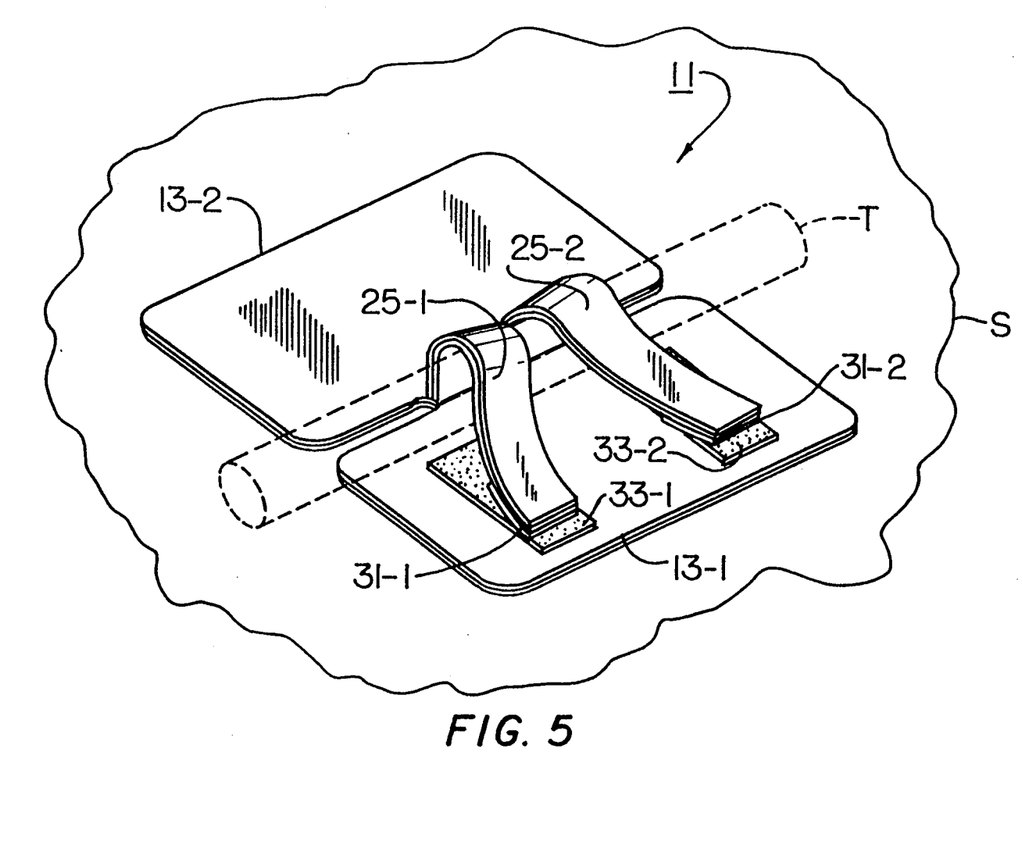
FIG. 5 is a perspective view showing a third way in which the device of FIG. 1 may be used to secure a catheter tube (shown in phantom) to a surface.

To use device 11 to secure generally tubular member T to a support surface S in the manner shown in FIG. 5, tubular member T is first positioned so that it extends across first segment 13-1. Tabs 25-1 and 25-2 are then looped over tubular member T, and first fastening means 31-1 and 31-2 are brought into secure engagement with complementary fastening means 33-1 and 33-2, respectively.

When used as shown in FIG. 5, device 11 tends to restrain movement of the generally tubular member T primarily in the lateral direction (the extent of the restraint being dependent upon the closeness of the fit between the loops formed by tabs 25 and the diameter of tubular member T). Because the loops formed by tabs 25-1 and 25-2 are larger when device 11 is used in the manner shown in FIG. 5 than when device 11 is used in the same manner as shown in FIGS. 3 and 4, tubular members of greater diameter may be secured to a support structure when device 11 is used as shown in FIG. 5 than when device 11 is used as shown in FIGS. 3 and 4.

When device 11 is used in any of the ways described above to secure a generally tubular member T to a support surface S, first fastening means 31-1 and 31-2 may be repeatedly connected and disconnected to complementary fastening means 33-1 and 33-2, respectively, without losing their fastening ability. Consequently, tubular member T may be repeatedly removed and resecured to device 11 for adjustment or other purposes without requiring the removal of device 11 from support surface S.

Figure 6:
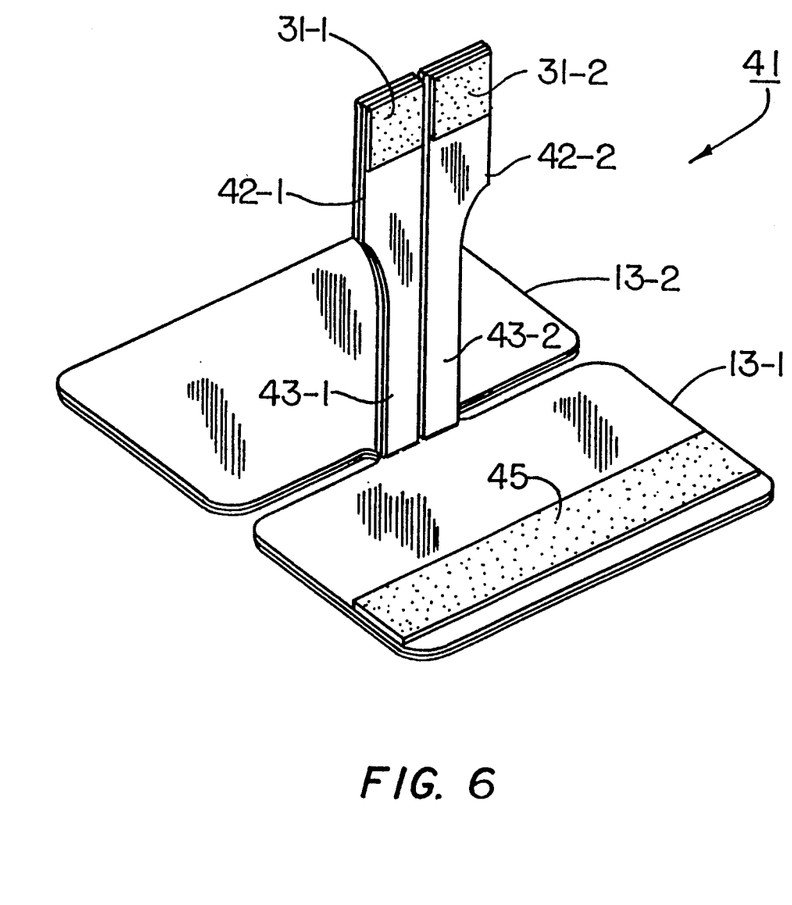
FIG. 6 is a perspective view of a second embodiment of a device constructed according to the teachings of the present invention for securing a generally tubular member of a medical appliance to a support surface.

Referring now to FIG. 6, there is shown a perspective view of a second embodiment of a device constructed according to the teachings of the present invention for securing a generally tubular member of a medical appliance to a support surface, the device being represented generally by reference numeral 41.

Device 41 is generally similar in size, shape and construction to device 11 and may be used in at least the three ways described above in connection with device 11. The principal differences between device 11 and device 41 are that (1) flexible retaining tabs 42-1 and 42-3 of device 41 have inwardly tapering connected ends 43-1 and 43-2, respectively, to prevent buckling of tabs 42-1 and 42-2 when they are wrapped around the circumference of a generally tubular member and secured to first segment 13-1 in the manner shown in FIGS. 3 and 4; and (2) a single complementary fastening means 45 is mounted across the length of segment 13-1.

Figure 7:
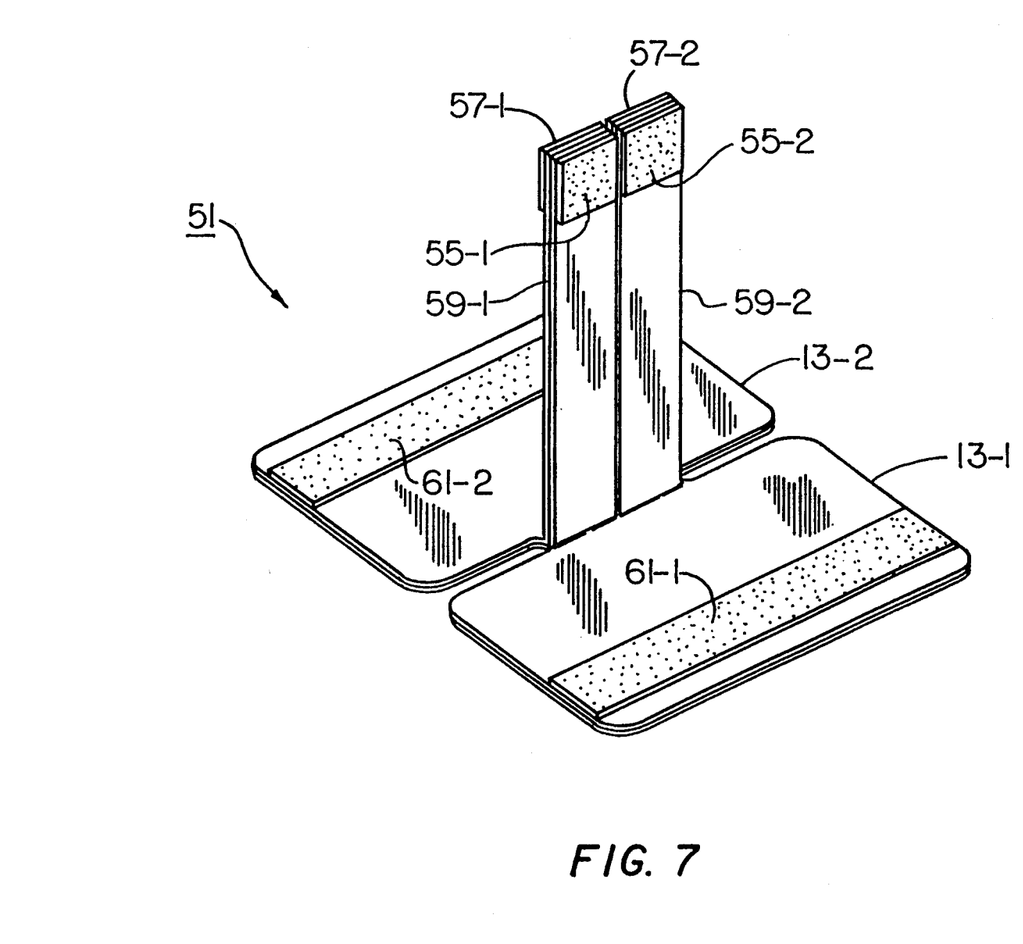
FIG. 7 is a perspective view of a third embodiment of a device constructed according to the teachings of the present invention for securing a generally tubular member of a medical appliance to a support surface.

Referring now to FIG. 7, there is shown a perspective view of a third embodiment of a device constructed according to the teachings of the present invention for securing a generally tubular member of a medical appliance to a support surface, the device being represented by reference numeral 51.

Device 51 is generally similar in size, shape and construction to device 11 and may be used in at least the same ways. The principal differences between device 51 and device 11 are that (1) first fastening means 55-1/55-2 and 57-1/57-2 are mounted on opposite sides of flexible retaining tabs 59-1 and 59-2, respectively; and (2) complementary fastening means 61-1 and 61-2 are mounted across the length of segments 13-1 and 13-2, respectively.

Figure 8:
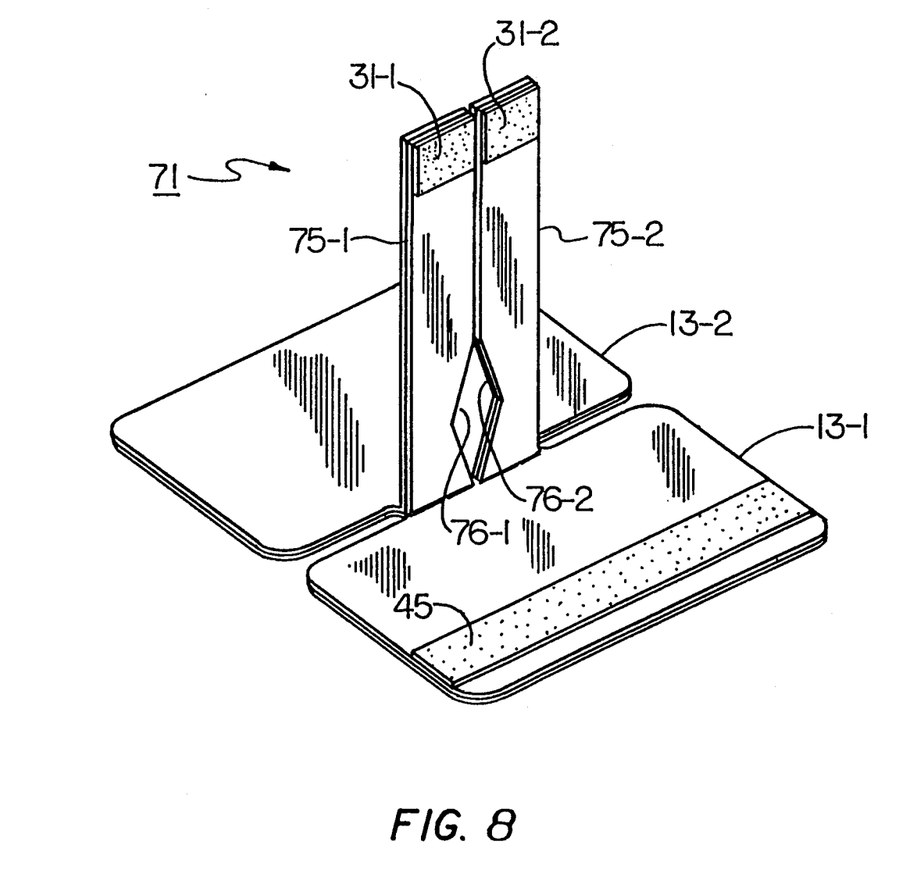
FIG. 8 is a perspective view of a fourth embodiment of a device constructed according to the teachings of the present invention for securing a generally tubular member of a medical appliance to a support surface.

Referring now to FIG. 8, there is shown a perspective view of a fourth embodiment of a device constructed according to the teachings of the present invention for securing a generally tubular member of a medical appliance to a support surface, the device being represented by reference numeral 71.

Device 71 is generally similar in size, shape and construction to device 41 and may be used in at least the same ways. The principal difference between device 71 and device 11 is that flexible retaining tabs 75-1 and 75-2 of device 71 have cut-away portions 76-1 and 76-2, respectively, to prevent buckling of tabs 75 when they are wrapped around the circumference of a generally tubular member and secured to segment 13-1 in the same manner as shown in FIGS. 3 and 4.

Figure 9:
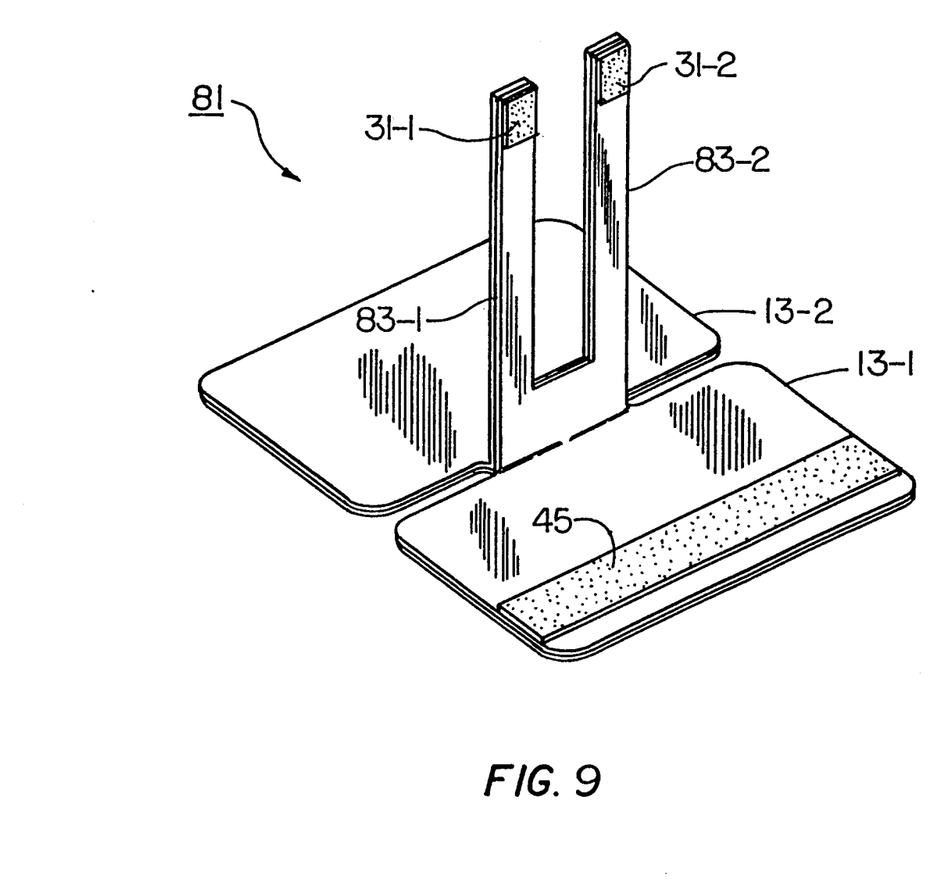
FIG. 9 is a perspective view of a fifth embodiment of a device constructed according to the teachings of the present invention for securing a generally tubular member of a medical appliance to a support surface.

Referring now to FIG. 9, there is shown a perspective view of a fifth embodiment of a device constructed according to the teachings of the present invention for securing a generally tubular member of a medical appliance to a support surface, the device being represented by reference numeral 81.

Device 81 is generally similar in size, shape and construction to device 41 and may be used in at least the same ways. The principal difference between device 81 and device 11 is that flexible retaining tabs 83-1 and 83-2 of device 81 (1) are more narrow than tabs 25-1 and 25-2 of device 11, (2) are spaced apart slightly, and (3) are joined together at their respective connected ends to form a U-shaped member.

Figure 10:
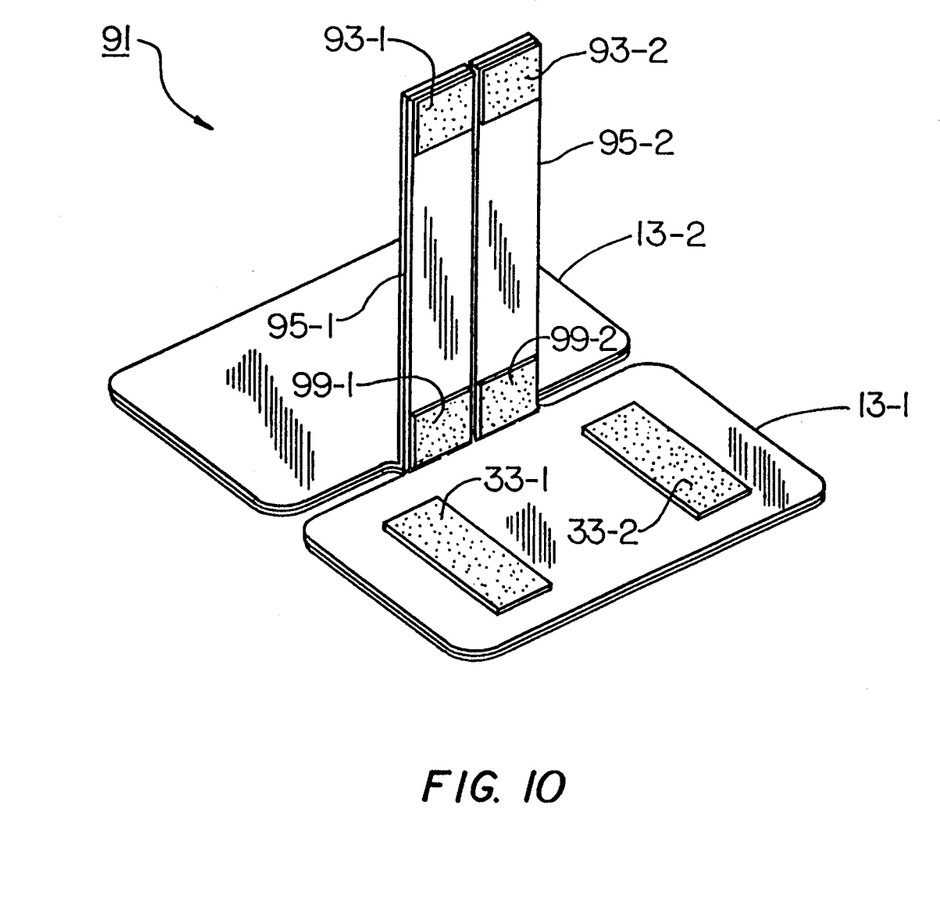
FIG. 10 is a perspective view of a sixth embodiment of a device constructed according to the teachings of the present invention for securing a generally tubular member of a medical appliance to a support surface.

Referring now to FIG. 10, there is shown a perspective view of a sixth embodiment of a device constructed according to the teachings of the present invention for securing a generally tubular member of a medical appliance to a support surface, the device being represented by reference numeral 91.

Device 91 is generally similar in size, shape and construction to device 11. The principal difference between device 91 and device 11 is that device 91, in addition to including first fastening means 93-1 and 93-2 mounted on the respective free ends of flexible retaining tabs 95-1 and 95-2 and complementary fastening means 97-1 and 97-2 mounted on first segment 13-1, additionally includes second complementary fastening means 99-1 and 99-2 mounted on the respective connected ends of tabs 95-1 and 95-2. Consequently, device 91 may be used to secure a generally tubular member to a support surface in the same manner as shown in FIGS. 3 through 5 or, alternatively, may be used as follows: with the generally tubular member extended across tabs 95-1 and 95-2, first fastening means 93-1 and 93-2 are brought into secure engagement with second complementary fastening 99-1 and 99-2, respectively.

Figure 11:
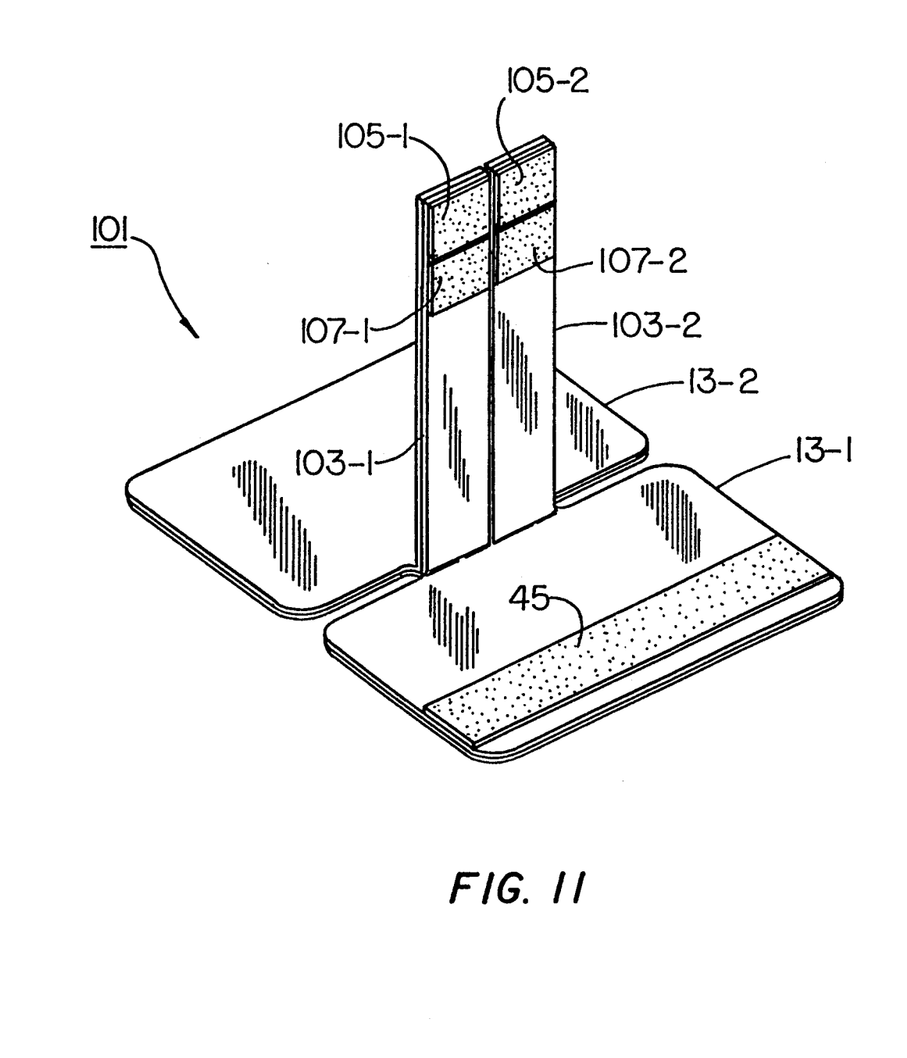
FIG. 11 is a perspective view of a seventh embodiment of a device constructed according to the teachings of the present invention for securing a generally tubular member of a medical appliance to a support surface.

Referring now to FIG. 11, there is shown a perspective view of a seventh embodiment of a device constructed according to the teachings of the present invention for securing a generally tubular member of a medical appliance to a support surface, the device being represented by reference numeral 101.

Device 101 is generally similar in size, shape and construction to device 41 and may be used in at least the same ways. The principal difference between device 101 and device 41 is that flexible retaining tabs 103-1 and 103-2 each have mounted thereon a pair of first fastening means 105-1/107-1 and 105-2/107-2, respectively. Accordingly, by selectively coupling either fastening means 105-1 and 105-2 or fastening means 107-1 and 107-2 to complementary fastening means 45, tubular members of a wider range of diameters may be secured thereby.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A device for securing a generally tubular member of a medical appliance to a support surface, said device comprising:
   a) an anchoring patch, said anchoring patch having a top surface and a bottom surface, said bottom surface being coated with an adhesive for attaching said anchoring patch to the support surface, said anchoring patch also including a first segment and a second segment, said first segment and said second segment each having an inner edge;
   b) a pair of flexible retaining tabs, each of said flexible retaining tabs being independently operable and having a first end and a second end, said first ends being connected to said anchoring patch and wherein said flexible retaining tabs interconnect and extend from said inner edges of said first segment and said second segment; and
   c) first fastening means secured to said second ends of said flexible retaining tabs and complementary fastening means secured to said top surface of said anchoring patch, said first fastening means and said complementary fastening means being positioned so that their joinder forms a pair of separable loops within which the generally tubular member of the medical appliance may be retained.

2. The device as claimed in claim 1 further comprising second complementary fastening means secured to said flexible retaining tabs, said second complementary fastening means being positioned so that they may be joined to said first fastening means to form a pair of separable loops within which the generally tubular member of the medical appliance may be retained.

3. The device as claimed in claim 1 wherein said first ends of said flexible retaining tabs are shaped to minimize buckling of said flexible retaining tabs should said flexible retaining tabs be coiled around the circumference of the generally tubular member of the medical appliance and secured to the top surface of said anchoring patch.

4. The device as claimed in claim 3 wherein said first ends of said flexible retaining tabs are narrower than said second ends.

5. The device as claimed in claim 3 wherein said flexible retaining tabs are outwardly-tapering from said first ends.

6. The device as claimed in claim 1 wherein said first fastening means comprises hook or loop fastening material and wherein said complementary fastening means comprises complementary hook or loop fastening material.

7. The device as claimed in claim 1 wherein said anchoring patch is wider than the combined width of said pair of flexible retaining tabs.

8. The device as claimed in claim 7 wherein said complementary fastening means comprises two strips of fastening material extending transversely across said anchoring patch.

9. The device as claimed in claim 7 wherein said complementary fastening means comprises a single strip of fastening material extending across the length of said anchoring patch.

10. A device for securing a generally tubular member of a medical appliance to a support surface, said device comprising:
    a) an anchoring patch, said anchoring patch comprising a first segment and a second segment and, said first segment and said second segment each having an inner edge, having a top surface and a bottom surface, said bottom surface being coated with an adhesive for attaching said anchoring patch to the support surface;
    b) a flexible retaining tab extending from and interconnecting said inner edges of said first segment and said second segment, said flexible retaining tab having a first end and a second end, said first end being connected to said anchoring patch, said second end having a first side facing said first segment and a second side facing said second segment; and
    c) first fastening means secured to said first side and said second side of said second end and complementary fastening means secured to the top surface of said first segment and said second segment.

11. A device for securing a generally tubular member of a medical appliance to a support surface, said device comprising:
    a) an anchoring patch, said anchoring patch comprising a first segment and a second segment, said first segment and said second segment each having an inner edge, and having a top surface and a bottom surface, said bottom surface being coated with an adhesive;
    b) a flexible retaining tab extending from and interconnecting said inner edges of said first segment and said second segment, said flexible retaining tab being narrower than said first and second segments of said anchoring patch and having a first end and a second end, said first end being connected to said anchoring patch and being narrower than said second end, said flexible retaining tab not having any apertures through which said second end may be inserted; and
    c) first fastening means secured to said second end of said flexible retaining tab and complementary fastening means secured to the top surface of said first segment of said anchoring patch, said first fastening means and said complementary fastening means being positioned so that they may be joined together to form a separable loop within which the generally tubular member of the medical appliance may be retained.

12. The device as claimed in claim 11 wherein said complementary fastening means is positioned off to the side of said flexible retaining tab.

13. The device as claimed in claim 11 wherein said complementary fastening means extends substantially across the length of said first segment.

14. The device as claimed in claim 11 wherein said flexible retaining tab is outwardly-tapering from said first end.

15. The device as claimed in claim 11 wherein said flexible retaining tab has a straight edge and a curved edge.

16. A method of securing a generally tubular member of a medical appliance to a support surface, said method comprising the steps of:
    a) providing a device comprising:
       i) an anchoring patch mountable on a support surface, said anchoring patch comprising a first segment and a second segment, said first segment and said second segment each having an inner edge,
       ii) a flexible retaining tab extending from and interconnecting said inner edges of said first segment and said second segment, said flexible retaining tab having a first end and a second end, said first end being connected to said anchoring patch and being oriented generally parallel to said inner edges of said first segment and said second segment, said flexible retaining tab being of sufficient length to be wrapped around the circumference of the generally tubular member with said second end contacting the top surface of said anchoring patch, said flexible retaining tab not having any apertures through which said second end may be inserted, iii) first fastening means secured to said second end of said flexible retaining tab and complementary fastening means secured to said top surface of said anchoring patch, said first fastening means and said complementary fastening means being positioned so that said flexible retaining tab may be wrapped around the circumference of the generally tubular member and so that said first fastening means may be firmly and removably secured to said complementary fastening means;

b) wrapping said flexible retaining tab around the circumference of the generally tubular member; and c) bringing said first fastening means into secure engagement with said complementary fastening means.

17. A device for securing a generally tubular member of a medical appliance to a support surface, said device comprising:

a) an anchoring patch, said anchoring patch having a top surface and a bottom surface, said bottom surface being coated with an adhesive for attaching said anchoring patch to the support surface;

b) a pair of flexible retaining tabs, each of said flexible retaining tabs being independently operable and having a first end and a second end, said first ends being connected to said anchoring patch and wherein said first ends of each of said flexible retaining tabs are shaped to include a straight inner edge and a curved outer edge to minimize buckling of said flexible retaining tabs should said flexible retaining tabs be coiled around the circumference of the generally tubular member of the medical appliance and secured to the top surface of said anchoring patch; and c) first fastening means secured to said second ends of said flexible retaining tabs and complementary fastening means secured to said top surface of said anchoring patch, said first fastening means and said complementary fastening means being positioned so that their joinder forms a pair of separable loops within which the generally tubular member of the medical appliance may be retained.

* * * * *